United States Patent [19]

Miller et al.

[11] Patent Number: 5,591,839
[45] Date of Patent: Jan. 7, 1997

[54] POLYNUCLEOTIDES ENCODING α2-3 NEURAMINIDASE

[75] Inventors: Harvey I. Miller, Pleasant Hill; John C. Klock, Nicasio; Christopher M. Starr, Sonoma, all of Calif.

[73] Assignee: Glyko, Inc., Novato, Calif.

[21] Appl. No.: 294,477

[22] Filed: Aug. 18, 1994

[51] Int. Cl.$^6$ .......................... C07H 21/02; C07H 21/04
[52] U.S. Cl. .......................... 536/23.7; 536/23.2
[58] Field of Search .......................... 536/23.7, 23.2, 536/23.4; 435/320.1, 252.3, 252.33

[56] References Cited

U.S. PATENT DOCUMENTS 4,071,408  1/1978  Flashner et al. .......................... 195/62

OTHER PUBLICATIONS

Yeung et al, Applied. Envir. Microbiol 57: 3062–3069 (1991).
Davis et al, PNAS 80: 3976–3980 (1983).
Rademacher et al., *Ann. Rev. Biochem.*, 57:789:838 (1988).
Advertisement entitled, "With Glyco FACE technology you can separate, quantify, or sequence your carbohydrate . . . In one day.," *Nature*, vol. 364, No. 6437, Reader Service No. 356 (Aug. 5, 1993).

Glyko, Inc., Product Specification for "NANase I . . . a recombinant glycosidase specific for α2–3 linked N–acetyl-neuraminic acid", pp. 1–2 (Jun. 20, 1994).

*Primary Examiner*—Stephanie W. Zitomer
*Assistant Examiner*—Eggerton Campbell
*Attorney, Agent, or Firm*—Albert P. Halluin, Esq.; Pennie & Edmonds

[57] ABSTRACT

Polynucleotide sequences encoding enzymes that possess α2-3 neuraminidase activity are provided. Of particular interest are polynucleotide sequences encoding an enzyme having α2-3 neuraminidase activity and naturally produced by the bacteria *Streptococcus pneumoniae*. Recombinant DNA expression of enzymes possessing α2-3 specific neuraminidase activity is also described, including methods, recombinant host cells and a genetic construction. The invention also provides a purified enzyme having α2-3 neuraminidase activity from *Streptococcus pneumoniae*, wherein the enzyme is isolated from *S. pneumoniae* cultures. Another aspect of this invention is to provide methods of isolating genes encoding enzymes having neuraminidase activity, particularly α2-3 neuraminidase activity. The gene isolation methods of the invention comprise the step of labeling a hybridization probe derived from the neuraminidase coding portion of plasmid pND-1. The hybridization probe may then be used to isolate homologous genes encoding enzymes having the desired enzymatic activity.

10 Claims, No Drawings

POLYNUCLEOTIDES ENCODING α2-3 NEURAMINIDASE

FIELD OF THE INVENTION

This invention is in the field of the molecular biology, more particularly in the field of enzymes having neuraminidase activity.

BACKGROUND

Carbohydrates play a number of important roles in the functioning of living organisms. In addition to their metabolic roles, carbohydrates may be covalently attached to numerous other entities such as proteins and lipids, i.e., glycoconjugates. For example, the carbohydrate portion of glycoproteins may critically affect the ability of glycoproteins to perform their biological functions, including such functions as ligand or receptor recognition.

The enormous potential for chemical and structural diversity among carbohydrates is provided, in part, by the way in which individual sugar units in a polysaccharide can be linked. A fundamental step in determining the three-dimensional structure of a polysaccharide or oligosaccharide is to determine the structure of these linkages.

Many carbohydrate structures in nature are polysaccharides and oligosaccharides that are produced in a variety of related forms rather than existing in a single defined structure. These families of related carbohydrates are frequently found to be components of the same glycoconjugate. These families of glycoproteins that share the same polypeptide structure, but display variation in the glycosylation pattern have been referred to as glycoforms, Rademacher, et al., *Ann. Rev. Biochem.*, 57:789:838 (1988). Similarly, there is great diversity in the glycoforms associated with glycolipids, proteoglycans, and polysaccharides.

The elucidation of the structure of carbohydrates and various glycoconjugates is of considerable importance in both biological and medical research. The analysis of the structures of these molecules is largely dependent on the availability of enzymes that recognize specific structures within carbohydrate molecules, i.e., the enzymes are specific for specific linkages between specific subunits of complex carbohydrates. It is thus of interest to provide enzymes that are specific for certain carbohydrate structures so as to provide for the structural analysis of newly discovered carbohydrate molecules.

It is also of interest to provide for the production of substrate-specific carbohydrate hydrolyzing enzymes by means of recombinant DNA technology. Recombinant DNA technology allows the enzymes of interest to be produced in a form that is substantially free of contaminating enzyme activity that may mask the desired activity of the enzyme of interest.

One type of carbohydrate hydrolyzing enzyme of particular interest are the neuraminidases. Neuraminidases are capable of catalyzing the release of N-acetylneuraminic acid or other forms of neuraminic acid from complex carbohydrates. Different neuraminidases are specific for the release of N-acetylneuraminic acid depending upon the specific linkage between the N-acetylneuraminic acid and the rest of the complex carbohydrate. This application describes the first isolation and discovery of a neuraminidase specific for the α2-3 linkage between N-acetylneuraminic acid and a complex carbohydrate. Also described for the first time is the recombinant DNA production of an enzyme possessing neuraminidase activity.

SUMMARY OF THE INVENTION

The invention provides several polynucleotide sequences encoding enzymes that possess neuraminidase activity specific for the α2-3 linkage between N-acetylneuraminic acid and the remainder of a complex carbohydrate molecule, i.e., α2-3 neuraminidase activity. Of particular interest are polynucleotide sequences encoding an enzyme having α2-3 neuraminidase activity and naturally produced by the bacterium *Streptococcus pneumoniae.* The DNA sequence encoding this *S. pneumoniae* is present on plasmid pND-1 (ATCC deposit 97661).

Another aspect of the invention is to provide expression vectors for the recombinant DNA expression of enzymes possessing α2-3 specific neuraminidase activity.

Another aspect of the invention is to provide recombinant host cells for the production of enzymes possessing α2-3 neuraminidase activity. The host cells of the invention comprises a genetic construction that comprises a polynucleotide sequence encoding an enzyme possessing α2-3 neuraminidase activity. Of particular interest are host cells for the production of the neuraminidase encoded by the plasmid pND-1.

Another aspect of the invention is to provide methods for the production of enzymes possessing α2-3 neuraminidase activity by recombinant DNA methodology. These methods typically involve the step of preparing a lysate from the recombinant host cells of the invention. Another aspect of the invention is to provide lysates of such recombinant host cells.

Another aspect of the invention is to provide a purified enzyme having α2-3 neuraminidase activity from *Streptococcus pneumoniae,* when the enzyme is isolated from *S. pneumoniae* cultures.

Another aspect of this invention is to provide methods of isolating genes encoding enzymes having neuraminidase activity, particularly α2-3 neuraminidase activity. The gene isolation methods of the invention typically comprise the step of nucleic acid hybridization using a hybridization probe derived from, i.e., comprising at least a portion of, the neuraminidase coding portion of plasmid pND-1. The hybridization probe may then be used to isolate homologous genes encoding enzymes having the desired enzymatic activity.

DESCRIPTION OF THE SPECIFIC EMBODIMENTS

Definitions

As used herein, the term "neuraminidase activity" refers to the enzymatic activity that can catalyze the hydrolytic cleavage of N-acetylneuraminic acid from the non-reducing end of a carbohydrate chain. The carbohydrate chain substrate may be part of a complex carbohydrate, i.e, an oligosaccharide or larger carbohydrate. The carbohydrate chain substrate may also be the carbohydrate moiety of a glycoconjugate such as a glycoprotein or a glycolipid. The term "α2-3" as used herein in reference to an enzyme having neuraminidase activity indicates that the neuraminidase can catalyze an α2-3 linkage between N-acetylneuraminic acid and the adjoining portion of the larger carbohydrate. Unless indicated otherwise, the term "α2-3 neuraminidase activity" refers to activity significantly more specific for an α2-3 linkage, as opposed to other linkages between N-acetylneuraminic acid and the carbohydrate chain.

The Invention

The invention provides various polynucleotide sequences encoding enzymes having α2-3 neuraminidase activity, as well as host cells for producing the enzymes encoded by the polynucleotide sequence. Described herein, for the first time, is the discovery and purification of an enzyme having α2-3 neuraminidase activity, the cloning of an enzyme having α2-3 neuraminidase activity, and the recombinant DNA expression of an enzyme possessing α2-3 neuraminidase activity. Specifically, the application describes the discovery of an enzyme from *Streptococcus pneumonias* having α2-3 neuraminidase activity and the isolation of the gene encoding the enzyme, which is present on plasmid pND-1 (ATTC deposit 97661).

The invention provides for the polynucleotides encoding the enzyme possessing α2-3 neuraminidase activity encoded by plasmid pND-1 (ATTC deposit 97661). The sequence of the polynucleotide encoding this enzyme may be obtained by sequencing the DNA insert, i.e., the non-vector portion, of plasmid pND-1. DNA sequencing procedures suitable for obtaining this polynucleotide sequence are well known to the person of ordinary skill in the art of molecular biology. The region of the pND-1 plasmid to be sequenced may be reduced by subcloning. The precise nucleotide sequence encoding the enzyme possessing α2-3 neuraminidase activity encoded by pND-1 can be obtained by reviewing the information obtained by DNA sequencing so as to determine the open reading frames of the enzyme for determining the nucleotide sequence encoding a protein of interest on a plasmid known to encode the protein are well known to the person of ordinary skill in the art; examples of these techniques can be found, among other places, in Sambrook, et al., *Molecular Cloning: A Laboratory Manual, 2nd Ed.* Cold Spring Harbor Press, Cold Spring Harbor (1989), Ausubel, et al., *Short Protocols In Molecular Biology, 2nd Ed.*, Academic Press, San Diego (1992), Berger and Kimmel *Guide to Molecular Cloning Techniques,* Academic Press, San Diego (1987), and the like. The amino acid sequence of the enzyme possessing α2-3 neuraminidase activity encoded by plasmid pND-1 may readily be determined by analyzing the coding polynucleotide sequence using methods that are well known to the person of ordinary skill in the art.

The amino acid sequence of the neuraminidase encoded by pND-1 and the naturally occurring polynucleotide sequences encoding the neuraminidase encoded by pND-1 enable a person of ordinary skill in the art of molecular biology to design and construct a variety of related molecules having useful properties similar to the neuraminidase encoded by pND-1 and naturally occurring polynucleotides encoding the enzyme. In the case of polynucleotides, the degeneracy of the genetic code permits the person of ordinary skill in the art to produce numerous different polynucleotides encoding the same polypeptide, i.e., isocoding polynucleotides. The precise polynucleotide sequence produced may be selected so as to optimize expression in a particular host cell type, taking into account factors affecting expression such as codon frequency, potential mRNA secondary structures, methylation sites, and the like. The invention also provides a variety of polypeptides having the same α2-3 neuraminidase activity as the neuraminidase encoded by pND-1, but differing in one or more amino acid residues, so as to produce a variant polypeptide. Variants of the neuraminidase encoded by pND-1 may be produced and designed in a wide variety of methods. Variants may be produced and designed by introducing mutations (either random or by design) into a polynucleotide sequence encoding the neuraminidase encoded by pND-1, transforming the mutated neuraminidase encoding polynucleotide (operably linked to a suitable promoter) into a host cell, and subsequently assaying the host cell for the expression of α2-3 neuraminidase activity. The identity of the randomly induced mutations in the neuraminidase encoding polynucleotides may be determined by sequencing the polynucleotide encoding the enzyme.

The invention also provides for expression vectors for the expression of enzymes possessing α2-3 neuraminidase activity in a host cell, preferably the vectors are for the α2-3 neuraminidase possessing enzyme encoded by pND-1. The expression vectors of the invention may be any of a variety of vectors suitable for genetically manipulating host cells, such as plasmids, cosmids, phagemids, retroviral vectors, and the like. The expression vectors of the invention comprise a polynucleotide sequence encoding an enzyme possessing α2-3 neuraminidase activity and promoter sequence in functional combination with the enzyme encoding sequence. The expression vectors of the invention may further comprise other nucleotide sequence influencing the expression of the enzyme such as, enhancers, regulatory sequences, leader sequences, and the like. Methods of making and using expression vectors to produce proteins heterologous with respect to a give host cell are well known to the person of ordinary skill in the art, examples of such methods can be found, among other places, in Goeddel, et al. *Gene Expression Technology: Methods In Enzymology, Volume 185,* Academic Press, San Diego (1991).

The invention also provides for the recombinant DNA expression of the neuraminidase encoded by pND-1 (as well as variants thereof). The recombinant expression of these enzymes may be achieved through standard recombinant DNA expression technology using expression vectors, as previously described. The enzyme may be expressed in a wide range of host cells, including both eukaryotic and prokaryotic host cells. One advantage of providing the subject enzymes by recombinant DNA methodology is the production of increased amounts of enzyme from reduced amounts of cellular material and enzymes having unwanted activity. The α2-3 neuraminidase encoded by pND-1 and variants thereof may be purified by procedures similar to the procedures explicitly described in the examples given below and numerous variations of these procedures that would be appreciated by the person of ordinary skill in the art. Guidance in devising and modifying enzyme purification procedures can be found, among other places in Deutscher *Guide to Protein Purification Methods in Enzymology—Volume* 182) Academic Press, San Diego (1990), Scopes *Protein Purification: Principles and Practice* 3*rd edition* Springer-Verlag, NY (1993), and the like. Typically, the purification procedures of the invention involve the steps of growing the host cell in culture and/or forming a cellular lysate when the enzyme having α2-3 neuraminidase is not secreted from the host cell. The lysate may be produced by a variety of methods that are, in part, dependent upon the particular host cell used. For example, lysates may be produced by sonication, non-ionic detergent solubilization, lysozyme digestion, and the like. Lysates of host cells producing enzymes having α2-3 neuraminidase activity are particularly useful because they may provide an enriched source of the enzyme.

The invention also provides various methods for the isolation of polynucleotide sequences encoding other enzymes having neuraminidase activity, including α2-3 neuraminidase activity. These methods involve the use of a nucleic acid hybridization probe or probes derived from the portion of plasmid pND-1 encoding the enzyme having α2-3 neuraminidase activity. The hybridization probe is then hybridized against DNA suspected of containing sequences bearing homology to the hybridization probe. The hybridization step may take many forms, such as the hybridization screening of genetic libraries, polymerase chain reaction (PCR) mediated amplification (the primers hybridize, i.e., anneal, to target sequences), and the like. The hybridization probe may also be labeled, either isotopically or non-isotopically. The hybridization step may take place under a variety of hybridization conditions, preferably the hybridization step takes place under stringent hybridization conditions. Additionally, the invention provides for methods of isolating polynucleotide sequences encoding enzymes having neuraminidase activity by using essentially the same genetic library screening method used for the isolation of pND-1 as described in the example given below, i.e., colony screening using a fluorescent substrate.

The invention also provides for a purified enzyme possessing $\alpha$2-3 neuraminidase activity that is naturally produced by *Streptococcus pneumoniae*. The enzyme may be produced by growing *S. pneumoniae*, preferably *S. pneumoniae* (ATCC deposit No. 33400) in culture and purifying the enzyme from the culture supernatant. The enzyme may be purified essentially as described in the examples, with the exception that a cell lysate need not produced, as the enzyme may be isolated from the culture supernatant.

EXAMPLES

The following examples are given to illustrate embodiments of the present invention as it is presently preferred in practice. It will be understood that these examples are illustrative of the invention and are not to be considered as limiting.

EXAMPLE 1

*Streptococcus pneumoniae* DNA Isolation

The DNA for literary formation was isolated from a cell pellet of *S. pneumoniae* ATCC #33400 was purchased from the ATCC (American Type Culture Collection). The cell pellet was thawed into 20 ml 50 mM Tris pH 8, 10 mM EDTA, 2 mg/ml egg white lysozyme and incubated on ice for 20 minutes. SDS was added to a final concentration of 0.1%. RNAase was added to a final concentration of 10 μg/ml. The mixture was incubated for 30 minutes at 37° C. 10 ml of buffer saturated phenol and 10 ml chloroform were then added. The mixture was vortexed for 1 minute. The mixture was then centrifuged for 10 minutes at 10K rpm in a Sorvall centrifuge. The top (aqueous) layer was then removed and retained. 40 ml cold ethanol was then added and the DNA was wound onto a glass pipette. The DNA was then dissolved in 1 ml of distilled water. The isolated DNA was then sheared by being forced through a 26 gauge hypodermic needle.

EXAMPLE 2

Genetic Library Formation

Ten μg of the purified *S. pneumoniae* DNA was added to a tube of restriction buffer #3 from New England Biolabs (NEB) in a total volume of 100 μl and heated to 37° C. Mbo I enzyme (5U) was added to the DNA and allowed to incubate for 5 min. EDTA is then added to a final concentration of 100 mM. Phenol and chloroform (50 μl each) were then added and the tube was vortexed for 1 min. The tube was centrifuged and the aqueous layer removed and saved. Cold ethanol (200 μl) and 10 μl 3M sodium acetate pH 7 were then added and the tube was incubated on ice for 5 minutes. The DNA was pelleted and the DNA pellet washed with 80% cold ethanol. The pellet was then dried in a Speed-Vac and then resuspended in 20 μl distilled water.

The DNA (10 μl) was added to a tube containing 20 μl of T-4 ligase buffer (New England Biolabs) and 10 ng of pGEM-3Z (described in Sambrook, et al., *Molecular Cloning: A Laboratory Manual, 2nd Ed.*, Cold Spring Harbor Press, Cold Spring Harbor (1989)), which had been cleaved with BamHI and treated with calf intestinal phosphatase. T4 DNA ligase was added and the reaction incubated at 14° C. for 16 hours. The ligation mixture (3 μl) was transformed into *E. coli* strain GS1 by electroporation and plated on LB agar plates containing 100 μg/ml ampicillin.

EXAMPLE 3

Screening For Neuraminidase Clones

Paper filters were saturated with a solution of 100 μM 4-methyumbelliferyl-N-acetylneuraminic acid in 50 mM sodium phosphate buffer pH 5. The filters were carefully placed on plates containing about 10,000 clones. The filters were peeled off the plates and observed colony side up under an ultraviolet light source. Colonies fluorescing white were picked with a sterile loop and purified by streaking on LB-AMP agar plates. One clone was chosen for a production strain. It contained a plasmid, which was named pND-1 which was 6.4 kilobase pairs of DNA, with an insert size of 3.7 kilobase pairs. The clone contained two EcoRI restriction enzyme recognition sites and EcoRI released 1.4 kilobase pair and 5 kilobase pair fragments.

EXAMPLE 4

Purification of Neuraminidase

A colony of *E. coli* containing pND-1 was grown in LB-AMP media to saturation at 37° C. The cells were pelleted and resuspended in 20 mM Tris pH 7.5, 25 mM NaCl (buffer A). The cells were then broken by sonic disruption. Cell debris was removed by centrifugation at 20,000 rpm in a Sorvall refrigerated centrifuge. To the supernatant, NaCl was added to 0.8M and polyethyleneimine was added to 0.1%. The extract was stirred on ice and centrifuged at 17,000 rpm for 10 minutes. To the supernatant, ammonium sulfate was added to 35% saturation. The precipitate was removed by centrifugation at 17,000 rpm for 10 minutes. To the supernatant, ammonium sulfate was added to 65% saturation. The mixture was then centrifuged at 17,000 rpm for 10 minutes and the pellet was saved. The pellet was resuspended in buffer A and dialyzed against buffer A (500 vol).

The dialyzed extract was applied to a column of Q-Sepharose equilibrated with buffer A. The column was washed extensively with buffer A. The neuraminidase was eluted from the column with a buffer consisting of 20 mM Tris pH 7.5, 100 mM NaCl.

EXAMPLE 5

Characterization of Cloned Neuraminidase

Assay for Neuraminidase

Neuraminidase was assayed using 250 mM 4-methylumbelliferyl-N-acetylneuraminic acid at pH5 in 50 mM sodium phosphate buffer at 37° C. One unit is defined as the amount of enzyme which will produce 1 μM of methyumblliferone in one minute at 37° C.

Molecular Weight of *Streptococcus pneumoniae* Neuraminidase

SDS polyacrylamide gel electrophoresis of purified neuraminidase reveals a single polypeptide with a relative molecular weight of about 80,000 daltons.

Linkage Specificity of Neuraminidase

The activity of the purified enzyme was determined by incubating the enzyme with various carbohydrates and assaying the carbohydrates for structural changes. The structural changes were assayed by fluorophore assisted carbohydrate electrophoresis (FACE®, Glyko Inc., Novato, Calif.). In fluorophore assisted carbohydrate electrophoresis carbohydrates are labeled with a charged fluorescent label and separated by migration in a gel in an electric field. Assays were performed using the fluorescent compound 8-aminonapthalene-1,3,6-trisulphonia acid (ANTS).

The following reaction tubes were set up (1) 3'-Sialyllactose (Neu5Acα2-3Galβ1-4Glc)

(2) 3'-Sialyllactose with the purified enzyme, (3) 6'-Sialyllactose (Neu5Acα2-6Galβ1-4Glc), (4) 6'-Sialyllactose with purified enzyme, (5) GD3 oligosaccharide (Neu5Acα2-8Neu5Acα2-3Galβ1-4Glc), and (6) GD3 oligosaccharide with purified enzyme. Fluorophore assisted carbohydrate electrophoresis was performed on the reaction tubes and control standards for anticipated reaction products. Only carbohydrates containing the α2-3 linkage were found to be cleaved by the purified enzyme.

Specific Activity of Neuraminidase

The neuraminidase has a specific activity of –200 U/mg protein. Protein concentration was assayed using Bradford's reagent with BSA as a standard.

INCORPORATION BY REFERENCE

All patents, patents applications, and publications cited are incorporated herein by reference.

EQUIVALENTS

The foregoing written specification is considered to be sufficient to enable one skilled in the art to practice the invention. Indeed, various modifications of the above-described makes for carrying out the invention which are obvious to those skilled in the field of organic chemistry or related fields are intended to be within the scope of the following claims.

What is claimed:

1. An isolated polynucleotide from a Streptococcus species encoding an enzyme possessing α2-3 neuraminidase activity.

2. A polynucleotide according to claim 1, wherein the isolated polynucleotide is present on plasmid pND-1.

3. An expression vector for the recombinant expression of an isolated polynucleotide from a Streptococcus species encoding an enzyme possessing α2-3 neuraminidase activity in a microbial host cell, said expression vector comprising, in functional combination:

a heterologous promoter sequence, and a polynucleotide for expression encoding an enzyme that possesses said enzymatic activity.

4. An expression vector according to claim 3, wherein the polynucleotide for expression hybridizes under stringent conditions to the portion of plasmid pND-1 that encodes an enzyme with said enzymatic activity.

5. An expression vector according to claim 4, wherein the polynucleotide for expression is present on plasmid pND-1.

6. A microbial host cell for the recombinant expression of an isolated polynucleotide from a Streptococcus species encoding an enzyme possessing α2-3 neuraminidase activity, wherein said host cell comprises a polynucleotide vector encoding an enzyme possessing said enzymatic activity.

7. A host cell according to claim 6, wherein the polynucleotide vector is an expression vector for the expression of an enzyme that possesses said enzymatic activity, said expression vector comprising, in functional combination:

a heterologous promoter sequence, and a polynucleotide for expression encoding an enzyme that possesses said enzymatic activity.

8. A host cell according to claim 7, wherein the polynucleotide vector is pND-1.

9. A cell lysate derived from a cell comprising a recombinant expression product from an isolated polynucleotide from a Streptococcus species encoding an enzyme possessing α2-3 neuraminidase activity, wherein said cell does not naturally produce the enzyme.

10. A cell lysate according to claim 9, wherein the enzyme is encoded on plasmid pND-1.

\* \* \* \* \*